United States Patent [19]

Alter

[11] Patent Number: 4,457,313
[45] Date of Patent: Jul. 3, 1984

[54] SHIELD PROTECTOR FOR ARTIFICIAL INSEMINATION AND CULTURE COLLECTION INSTRUMENTS

[75] Inventor: Richard R. Alter, Delavan, Wis.

[73] Assignee: Continental Plastics Corporation, Delavan, Wis.

[21] Appl. No.: 371,208

[22] Filed: Apr. 23, 1982

[51] Int. Cl.³ .............................................. A61M 37/02
[52] U.S. Cl. .................................... 128/759; 128/749; 604/187; 604/197; 604/199
[58] Field of Search ............... 128/1 R, 749, 756, 759; 604/3, 55, 93, 181, 184, 187, 192, 198, 200, 199, 236, 238, 240, 263, 201, 205

[56] References Cited

U.S. PATENT DOCUMENTS

| | | | |
|---|---|---|---|
| 3,050,060 | 8/1962 | Hoffman | 604/187 X |
| 3,354,881 | 11/1967 | Block | 604/199 X |
| 3,507,281 | 4/1970 | Cassov | 604/423 V |
| 3,513,830 | 5/1970 | Kalayjian | 128/759 |
| 3,890,971 | 6/1975 | Lesson et al. | 604/197 X |

FOREIGN PATENT DOCUMENTS

WO80/01353  7/1980  PCT Int'l Appl. ................. 128/756

Primary Examiner—Edward M. Coven
Attorney, Agent, or Firm—Emrich, Lee, Brown et al.

[57] ABSTRACT

A shield protector device for use with artificial insemination instruments and/or culture collection devices, consisting of an inner tubular portion movable relative to an outer tubular sheath protector portion, includes a cylindrical housing having a closed end, which is sealingly attached to the distal end of the outer tubular sheath protector portion. The closed end of the housing is scored to provide a break-away membrane when the closed end of the shield protector is engaged by the inner tubular portion to complete the insemination or culture collection process.

8 Claims, 11 Drawing Figures

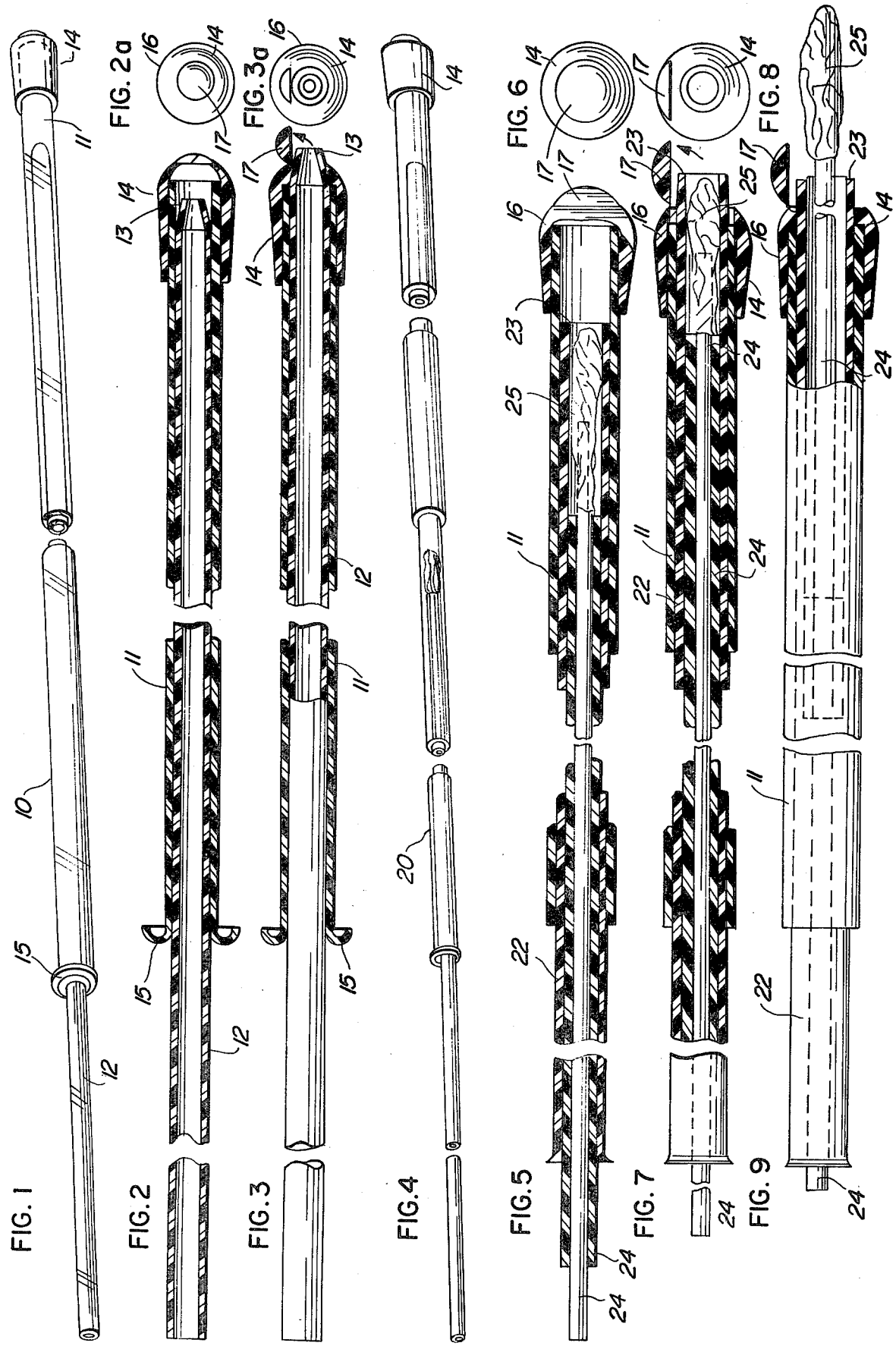

device includes a shield protector element sealingly mounted to the distal end of an outer sheath protector element which contains a slidable movable inner tubular swab protector which contains a slidably mounted swab or culture collection element. As set forth previously, upon insertion of the culture collection device past the vulva lining, and cervical canal into the cervix of the animal, the shield protector substantially eliminates diseases and contaminants from the vulva lining from being passed into the cervix of the animal and prevents contamination of the cultural gathering or swab tip contained within the cultural collection device. When the culture collection device has been fully inserted into the cervix of the animal, the inner tubular swab protector portion, containing the swab or cultural collections means therein, engages the scored end portion of the shield protector to break-away the protective scored end of the shield protector. Thereafter, the swab or cultural element device moves forward with respect to the inner tubular swab protector to culture the animal and/or apply medication to the cervix of the animal. Upon completion of this medicating and/or culture collecting process, the swab element is moved outwardly relative to the inner tubular swab protector to rest inside thereof and then the inner tubular protector is moved outwardly with respect to the outer sheath protector tube. Upon removal of the device from the animal, the shield protector prevents contamination of the swab or collection element from being contaminated by disease and unsanitary matter within the animal.

DESCRIPTION OF THE DRAWINGS

FIG. 1 is a perspective view of the artificial insemination instrument and shield protector device in accordance with the present invention;

FIG. 2 is a longitudinal cross-sectional view of the artificial insemination instrument and shield protector device in accordance with the present invention during insertion into the cervical canal of the animal;

FIG. 2a is an end view of the shield protector device mounted onto the sheath protector in accordance with the present invention;

FIG. 3 is a longitudinal cross-sectional view of the artificial insemination instrument and the shield protector device in accordance with the present invention;

FIG. 3a is an end view of the shield protector device in its open position when the instrument has been positioned in the cervix of an animal;

FIG. 4 is a perspective view of the cultural collection device and shield protector element in accordance with the present invention;

FIG. 5 is a longitudinal cross-section view of the culture collection device and protector shield element in accordance with the present invention during insertion of the device into the cervical canal of the animal;

FIG. 6 is an end view of the shield protector element mounted onto the culture collection device in accordance with the present invention of the embodiment as shown in FIG. 5;

FIG. 7 is a longitudinal cross-sectional view of the culture collection device and shield protector element in accordance with the present invention showing the scored portion of the element broken away upon engagement by the inner tubular swab protector;

FIG. 8 is an end view of the shield protector element showing the break-away scored portion of the shield protector element in the open position in accordance with the present invention; and FIG. 9 is a longitudinal cross-sectional view of the culture collection device and swab element fully extending outwardly from the scored portion of the shield protector element with the device is positioned in the cervix of the animal.

DETAILED DESCRIPTION

Referring now to the drawings wherein like numerals have been used throughout the several views to designate the same or similar parts, there is shown in FIG. 1 an artificial insemination instrument or device 10 which is comprised of an outer tubular sheath protector 11, an inner insemination tube 12 and a shield protector element 14.

The outer tubular sheath protector 11 includes a flange 15 at one end thereof with the shield protector element 14 sealingly attached to the opposite distal end. The inner insemination tube 12 contains the semen or, if desired, an antibiotic or other medication (not shown) which may be utilized in breeding the animal or medicating the animal for various and sundry diseases. The inner insemination tube 12 preferably includes a tapered end portion 13 which engages the shield protector element or device 14 to open the same, as will hereinafter be described.

The shield protector element or device 14 is composed of a soft vinyl material which is sealingly mounted to the outside surface of the outer tubular sheath protector 11. The cylindrical housing 16 of the shield protector element or device 14 having a scored end portion 17 which snaps and breaks-away upon engagement by the tapered end portion 13 of the insemination tube 12, when the insemination instrument has been positioned in the cervix of the animal. Although FIGS. 2a and 3a show that the scored end portion 17 of the shield protector element 14 is circular in shape, the scored configuration may be criss-crossed in form to permit the tapered end portion 13 of the insemination tube 12 to engage the closed end of the shield protector element and open the same with the shield protector element is scored.

It is further understood that the outer tubular sheath protector 11 may be of such a large inside diameter that the shield protector element or device 14 may be wedged within the inside surface thereof with a sufficient opening defined by the cylindrical housing to permit the tapered end portion 13 of the insemination tube 12 to extend therethrough to engage the closed end of the shield protector element and open the same where the shield protector is scored. Additionally, it is understood by scoring that the shield protector element 14 is partially cut or scored such that upon engagement by the tapered end portion 13 of the insemination tube 12, that the shield protector element acts as a breakable membrane to permit the scored portion 17 to break-away to an open position with the end 13 extending therethrough, as shown in FIG. 3 of the drawings.

In operating, the insemination instrument 10 is inserted into the vulva or cervical canal of the animal. The inner insemination tube 12 is pushed or moved forward relative to the outer tubular sheath protector 11, to a position as shown in FIG. 2. When the insemination instrument 10 has been fully positioned within the cervix, the tapered end portion 13 engages the scored end portion 17 of the shield protector element 14 to break-away the scored portion, a position as shown in

SHIELD PROTECTOR FOR ARTIFICIAL INSEMINATION AND CULTURE COLLECTION INSTRUMENTS

BACKGROUND OF THE INVENTION

The present invention relates to a break-away shield protector element for use with artificial insemination instruments and culture collection devices useful in medication, anticeptic or culture collection processes utilized in the animal husbandry industry.

During the insertion of artificial insemination instruments and/or cultural collection devices into the cervix of an animal, the instrument must pass through the vulva and/or cervical canal of the animal. Because the vulva and cervical canal are not sterile and most generally contain bacteria and diseased germs, such as vaginal or uterine infections or mycoplasma, it is vitally important to eliminate the transferral of these diseased germs and mycoplasma into the cervix. Moreover, because the insertion of insemination and collection control devices must pass through the cervical canal, oftentimes the prior art devices have carried and transported the diseased germs and contaminants from the cervical canal into the cervix during the artificial insemination process and/or the cultural collection process.

Prior art attempts to try to eliminate the transferral of contaminants and disease from the vulva and cervical canal to the cervix and to eliminate the contamination of the insemination instrument and/or cultural collection device during its passage through the cervical canal into the cervix are disclosed in Cassou U.S. Pat. No. 3,507,281 and Hoffman U.S. Pat. No. 3,050,060. However, in Cassou, the opening in the leading or distal end of the artificial insemination instrument permits the build-up of diseased germs and contaminants in the instrument during its insertion through the vulva and cervical canal and results in the semen or other material contained therein being contaminated during usage. Accordingly, such instruments, although reducing the amount of contaminants and disease carried into the cervix during usage, results in a use of an artificial insemination instrument which becomes contaminated during insertion into the cervix. Accordingly, such instruments have not solved the problem of eliminating the contamination of the semen during insertion into the cervix of the animal.

Similarly, the Hoffman patent discloses an artificial insemination instrument wherein the open ended sheath protector portion includes a cavity on the end thereof with a paper liner mounted therein. This cavity and liner structure, although reducing contamination of the semen contained in the insemination during insertion, provides a structure wherein the defined cavity collects diseased germs and transports them directly into the cervix of the animal. Accordingly, such an instrument and result is undesirable in artificial insemination and cultural collection devices.

Additionally, it has been suggested to mechanically fasten a blunt edged plug to the end of the artificial insemination instrument, such that after the instrument has been inserted within the cervix, the plug is pushed out and the insemination process is accomplished. However, such blunt edged plugs collect germs and unsanitary matter on the end thereof and transports them directly into the cervix of the animal. Moreover, when such instruments are removed from the animal, the mechanically fastening structure and trailing plug results in a structure which is injurious to the animal during usage.

SUMMARY OF THE INVENTION

It is an object of the present invention to provide a shield protector element on the operative and distal end of artificial insemination instruments and cultural collection devices which eliminates the transport of diseased germs, mycoplasm and unsterile matter from the vulva and cervical canal into the cervix and which eliminates the contamination of the semen or cultural collecting swab within the instrument during insertion into the cervix.

In one embodiment of the present invention, the novel shield protector element or means is attached to the operative or distal end of the outer sheath protector portion of an artificial insemination instrument. The shield protector element is comprised of soft vinyl tip material that sealingly engages about the outer surface of the operative or distal end of the tubular sheath protector portion of the insemination device. The shield protector element is, preferably, of tubular housing having the closed end partially scored to permit the inner insemination tube, which is slidingly movable within the outer tubular sheath protector, to engage the closed end of the shield protector and opened the same where the shield protector is scored.

The artificial insemination device in accordance with the present invention is comprised of an inner insemination tube portion slidably positioned within an outer tubular sheath protector portion, as is known in the art. The outer tubular sheath protector generally includes a flange on one end and the other distal end includes a plastic shield protector positioned thereon. The semen is positioned within the inner insemination tube and, upon the insertion of the insemination device into the vulva and cervical canal of the animal, as the insemination device passes through the vulva and cervical canal, the insemination tube is pushed forward relative to the sheet protector to engage the scored end portion of the shield protector element. After the insemination instrument is positioned in the cervix, the insemination tube engages and breaks-away the protective tip portion of the shield protector, thereby permitting the insemination tube to proceed to extend into the cervix during the infusion or insemination process. Preferably, the shield protector element or means is composed of a soft vinyl material to permit the scored closed end to act as a break-away membrane engaged with the tip end of the insemination tube. After the semen and, if desired, the antibiotics which may be added to the semen in an effort to control contamination by organisms or have been infused into the animal, the inner insemination tube is withdrawn outwardly relative to the outer sheath protector to a position within the shield protector and the entire insemination instrument is withdrawn from the animal to complete the insemination or infusion process. Upon withdrawl of the insemination device, the shield protector and its smooth configuration thereof, substantially reduces and eliminates any irritation or damage to the cervix, cervical canal and vulva lining of the animal. After removal of the insemination device, the device is discarded and the process is repeated upon subsequent animals.

In another embodiment of the present invention, the shield protector element or means is sealingly mounted to a culture collection device. The culture collection FIG. 3. Thereafter, the semen and, if desired, any antibiotics or other medication which may be added to the semen to control any possible disease in the animal, is infused or injected into the cervix of the animal. Thereafter, the inner insemination tube 12 is withdrawn relative to the outer sheath protector 11 to the position as shown in FIG. 2 and the insemination instrument 11 is withdrawn from the animal to complete the insemination or infusion process.

The tapered end portion 18 of the shield protector element 14 provides a tapered surface which prevents the transferral of diseased germs and unsanitary matter from the vulva lining and cervical canal from passing into the cervix of the animal during the insemination or infusion process. Thus, the mycoplasma infections contained in the vulva or cervical canal of the animal is prevented from being carried to and deposited in the cervix of the animal and prevents the source of infection or disease from attacking the animal during the insemination or infusion process. Additionally, the sealed shield protector element prevents the diseased germs and unsanitary matter contained in the vulva lining and cervical canal from penetrating the insemination instrument 10 and contaminating the semen and/or other medication contained therein. After removal of the insemination device from the animal, the device is discarded.

In another embodiment of the present invention, in FIG. 4, a shield protector element 17 is sealingly mounted to a culture collection device 20. As shown in FIGS. 4, 5, 7 and 9, the culture collection device 20 is comprised of an outer tubular sheath protector 11, an inner tubular swab protector 22 adapted for movement relative to the outer tubular sheath protector 11 and a tubular swab rod 24 having a swab 25 mounted to the end thereof. The tubular swab rod 24 is movable relative to the inner tubular swab protector 22, as will hereinafter be described. The shield protector element 14 is sealingly mounted to the outside surface of the tubular sheath protector 11 on the distal end thereof. As set forth previously with respect to the embodiment utilized on the insemination instrument 11 (FIGS. 1-3), the shield protector element or device 14 includes a cylindrical housing 16 having a scored closed end portion 17 (FIGS. 6, 6a) which snaps open or breaks-away upon engagement by the inner tubular swab end 23 of the tubular swab protector 22, when the culture collection device 20 has been positioned in the cervix of the animal. Although FIGS. 6 and 8 show that the scored end portions 17 of the shield protector element or device 14 is circular in shape, the scored configuration may be of criss-crossed design sufficient to permit the tubular swab end 23 of the tubular swab protector 22 to engage the closed end of the shield protector element and open the same when the shield protector element is scored. Preferably, the scored portion 17 is tapered outwardly to prevent build-up of materials therein during insertion into the cervix. Thus, in viewing the FIGS. 5 and 7, the tubular swab end 23 engages the scored portion 17 of the shield protector element 14 to snap open or break-away the scored portion 17 and move the same to an open position (FIG. 7) and to permit the inner tubular swab protector 22 to extend therethrough (FIG. 9). As shown in FIG. 9, the tubular swab rod mounting the swab 25 thereon, is then moved relative to the inner tubular swab protector 22 to collect the medical sample and/or medicate the cervix of the animal, as desired. After the medicating and/or collecting process has been completed, the swab and tubular swab rod 24 is pulled outardly relative to the inner tubular swab protector from a position as shown in FIG. 9 to a position as shown in FIG. 7. Thereafter, the inner tubular swab protector is pulled outwardly relative to the outer tubular sheath protector 11 to a position as shown in FIG. 5. The culture collection device 20 is then withdrawn from the animal to complete the medication or culturing process. Upon withdrawl of the culture collection device 20, the shield protector element 14 and its smooth configuration thereof substantially eliminates any irritation or damage to the cervix, the cervical canal and vulva lining and prevents disease or other contaminations from penetrating the collection device and damaging the culture obtained.

Thus, while I have illustrated and described the preferred embodiments of my invention, it is to be understood that this is capable of variation and modification, and I, therefore, do not wish to be limited to the precise details set forth, but desire to avail myself of such changes and alterations as fall within the purview of the following claims.

I claim:

1. A shield protector device for use with an artificial insemination instrument, said instrument including a tubular inner portion positioned within and movable relative to an outer tubular sheath protector portion having a distal end thereon said shield protector device including a cylindrical housing having a closed end, said cylindrical housing being sealingly mounted to said distal end of said outer tubular sheath protector portion and said closed end of said protector device is scored to provide a break-away membrane when said closed end of said shield protector is engaged by the end of the tubular inner portion to permit deposit of the semen into the cervix of an animal.

2. The shield protector device in accordance with claim 1 wherein said closed end of said cylindrical housing is tapered outwardly to facilitate insertion of the instrument into the cervix of an animal.

3. The shield protector device in accordance with claim 1 wherein said cylindrical housing is composed of plastic.

4. The shield protector device in accordance with claim 1 wherein said scored closed end is of a circular configuration having a diameter of at least the diameter of the tubular inner portion.

5. A shield protector device for use with a medicating collection instrument, said instrument including an inner tubular swab protector positioned within and movable relative to an outer tubular sheath protector having a distal end thereon, a tubular swab rod is positioned within and movable relative to said distal end of said outer tubular sheath protector and said closed end of said protector device is scored to provide a break-away membrane when said closed end of said shield protector is engaged by the end of the inner tubular swab protector to thereby permit said swab rod to be extended to collect the culture.

6. The shield protector device in accordance with claim 5 wherein said closed end of said cylindrical housing is tapered outwardly to facilitate insertion of the instrument into the cervix of an animal.

7. The shield protector device in accordance with claim 5 wherein said cylindrical housing is composed of plastic.

8. The shield protector device in accordance with claim 5 wherein said scored closed end is of a circular configuration having a diameter of at least the diameter of the inner tubular swab protector.

* * * * *